United States Patent [19]

Böger et al.

[11] Patent Number: 4,554,290
[45] Date of Patent: Nov. 19, 1985

[54] OXAMIC ACID DERIVATIVES

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 618,155

[22] Filed: Jun. 7, 1984

[30] Foreign Application Priority Data

Jun. 17, 1983 [CH]  Switzerland .......................... 3332/83

[51] Int. Cl.⁴ .................. C07C 125/065; A01N 47/10
[52] U.S. Cl. .................................... 514/487; 514/489; 560/9; 560/27; 560/164
[58] Field of Search .............................. 560/9, 27, 164; 424/300

[56] References Cited

U.S. PATENT DOCUMENTS

| | | | |
|---|---|---|---|
| 3,404,208 | 10/1968 | Robertson | 560/27 |
| 3,439,021 | 4/1969 | Fancher | 560/164 |
| 4,001,322 | 1/1977 | Marshall | 560/27 |
| 4,080,470 | 3/1978 | Karrer | 560/164 |
| 4,215,139 | 7/1980 | Fischer | 560/27 |
| 4,413,010 | 11/1983 | Zurfluh | 560/27 |

FOREIGN PATENT DOCUMENTS 0004334 10/1979 European Pat. Off. .
0072475 2/1983 European Pat. Off. .

*Primary Examiner*—Michael L. Shippen
*Attorney, Agent, or Firm*—Edward McC. Roberts

[57] ABSTRACT

There are disclosed novel oxamic acid esters substituted on the nitrogen atom and corresponding to the formula I

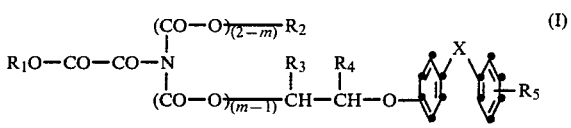

the production thereof, their use for controlling pests, and pesticidal compositions containing these oxamic acid esters as active ingredients. A preferred field of application is the control of pests on animals and plants, particularly of eggs and larvae of phytophagous insect pests and mites.

11 Claims, No Drawings

OXAMIC ACID DERIVATIVES

The present invention relates to novel oxamic acid esters substituted on the nitrogen atom, to the production thereof, to their use for controlling pests, and to pesticidal compositions containing these esters.

The compounds according to the invention correspond to the formula I $$R_1O-CO-CO-N\begin{array}{c}(CO-O)_{(2-m)}R_2\\ |\\ (CO-O)_{(m-1)}CH-CH-O-\end{array}\begin{array}{c}R_3\ R_4\\ |\ \ |\\ \end{array}\begin{array}{c}X\\ \end{array}R_5 \quad (I)$$

wherein
$R_1$ is $C_1-C_{10}$-alkyl,
$R_2$ is $C_1-C_4$-alkyl,
$R_3$ and $R_4$ are each hydrogen or methyl,
$R_5$ is hydrogen, halogen, $C_1-C_4$-alkyl, $C_1-C_4$-alkoxy, $C_1-C_4$-alkylthio or $C_1-C_4$-haloalkyl,
X is oxygen or sulfur, and
m is 1 or 2.

The $C_1-C_{10}$-alkyl groups denoted by $R_1$ can be branched-chain or straight-chain. Examples of such alkyl groups are, inter alia: methyl and ethyl as well as propyl, butyl, pentyl, hexyl, octyl or decyl, and isomers thereof. Preferred in this respect are $C_1-C_6$-alkyl groups, and amongst these the $C_1-C_4$-alkyl groups may in their turn be given particular mention.

The $C_1-C_4$-alkyl, -alkoxy, alkylthio- and -haloalkyl groups denoted by $R_2$ and $R_5$ can be branched-chain or straight-chain. Examples of such lower alkyl groups to be mentioned are: methyl and ethyl as well as propyl and butyl, and isomers thereof, methyl and ethyl being preferred.

The halogen substituents mentioned for $R_5$ are fluorine and chlorine and also bromine and iodine, fluorine and chlorine being preferred. This definition with regard to halogen applies also to the $C_1-C_4$-haloalkyl groups. Examples of such haloalkyl groups are, inter alia: the methyl group mono- to trisubstituted by fluorine, chlorine and/or bromine; the ethyl roup mono- to pentasubstituted by fluorine, chlorine and/or bromine; or the propyl group mono- to sevenfold-substituted by fluorine, chlorine and/or bromine.

Preferred compounds of the formula I are those wherein
$R_1$ is $C_1-C_6$-alkyl,
$R_2$ is $C_1-C_4$-alkyl,
$R_3$ and $R_4$ are each hydrogen or methyl,
$R_5$ is hydrogen or halogen,
X is oxygen or sulfur, and
m is 1 or 2.

Compounds of the formula I deserving special mention are those wherein
$R_1$ and $R_2$ are each $C_1-C_4$-alkyl,
$R_3$ and $R_4$ are each hydrogen or methyl,
$R_5$ is hydrogen or chlorine,
X is oxygen or sulfur, and
m is 1 or 2.

Of particular importance are above all the compounds of the formula I wherein
$R_1$ and $R_2$ are each methyl or ethyl,
$R_3$, $R_4$ and $R_5$ are each hydrogen,
X is oxygen, and
m is 2.

The compounds according to the present invention are produced in a manner known per se by for example reaction of a carbamic acid ester of the formula II $$HN\begin{array}{c}(CO-O)_{(2-m)}R_2\\ |\\ (CO-O)_{(m-1)}CH-CH-O-\end{array}\begin{array}{c}R_3\ R_4\\ |\ \ |\\ \end{array}\begin{array}{c}X\\ \end{array}R_5 \quad (II)$$

with an oxalic acid ester chloride of the formula III $$R_1O-CO-CO-Hal \quad (III)$$

In the formulae II and III, the symbols $R_1$, $R_2$, $R_3$, $R_4$, $R_5$, X and m have the meanings defined under the formula I, and Hal is fluorine, chlorine or bromine. The reaction is performed advantageously in the presence of an inert diluent, preferably an organic solvent, and optionally of a basic substance. In general, the reaction is carried out between 0° C. and the boiling temperature of the reaction mixture, preferably between room temperature and the boiling temperature.

Suitable inert organic solvents are in particular: (a) ethers and ethereal compounds, such as diethyl ether, 1,2-dimethoxyethane, tert-butylmethyl ether, dioxane or tetrahydrofuran; (b) hydrocarbons, for example n-hexane, benzene, toluene or xylenes; (c) halogenated hydrocarbons, for example methylene chloride, ethylene chloride, chloroform or carbon tetrachloride; (d) ketones, such as acetone, 2-butanone or 3-pentanone; (e) nitriles, for example acetonitrile or propionitrile; and (f) formamides, such as dimethylformamide.

Suitable basic substances are inorganic or organic acid binders, for example carbonates and bicarbonates of alkali metals and alkaline-earth metals, especially sodium or potassium carbonate or sodium bicarbonate, lower tertiary alkylamines, particularly trimethylamine or cycloalkylamine, especially pyridineor 1,4-diazabicyclo(2,2,2)octane.

The compounds of the formulae II and III used as starting materials are known, or they can be produced by known methods, for example from the corresponding carboxylic acid halides and amines.

With favourable tolerance to warm-blooded animals and to plants, the compounds according to the invention are valuable active substances for controlling pests. The compounds of the formula I are thus suitable for example for controlling pests on animals and plants. Such pests belong principally to the Arthropoda phylum, such as in particular insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera; and Arachnida of the order Acarina, for example mites and ticks. Every development stage of the pests can be controlled, that is to say, the adults, pupae and nymphs and also in particular the larvae and eggs. It is thus possible to effectively control especially larvae and eggs of phytophagous insect pests and mites in crops of ornamental plants and productive plants, for example in cotton and vegetable crops and particularly in fruit crops. When compounds of the formula I are taken up with the feed by imagines, the action of the compounds is shown by the immediate destruction of the pests or by a reduced oviposition and/or a lessened rate of hatching. The last-mentioned effect can be observed especially in the case of Coleoptera. In the control of zooparasitic pests, particularly on domestic and productive animals, the pests concerned are above all ectoparasites, for example mites and ticks and Diptera, such as *Lucilia sericata*.

The action of the compounds according to the invention, or of compositions containing them, can be considerably broadened and adaped to suit given circumstances by the addition of other insecticides and/or acaricides. Suitable additives are for example: organic phosphorus compounds, nitrophenols and derivatives thereof, formamidines, ureas, carbamates, pyrethroids, chlorinated hydrocarbons and *Bacillus thuringiensis* preparations.

The compounds of the formula I can be combined with particular advantage also with substances which intensify pesticidal activity. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I are used either in an unmodified form or preferably together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, and likewise the type of compositions, are selected to suit the objectives to be achieved and the given conditions.

The formulations, that is to say, the compositions or preparations containing the active ingredient of the formula I, or combinations of this active ingredient with other insecticides or acaricides, and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers.

Suitable granulated absorptive carriers are porous types, for example: pumice, ground brick, sepiolite or bentonite; and suitable nonsorbent carriers are materials such as calcite or sand. A great number of pre-granulated materials of inorganic or organic nature, such as in particular dolomite or ground plant residues, can also be used.

Depending on the nature of the active ingredient of the formula I, or of the combination of this active ingredient with other insecticides or acaricides, to be formulated, suitable surface-active compounds are: nonionic cationic and/or anionic tensides having good emulsifying, dispersing and wetting properties. By 'tensides' are also meant mixtures of tensides.

Suitable anionic tensides are both so-called water-soluble soaps, as well as water-soluble, synthetic, surface-active compounds.

Soaps which may be mentioned are the alkali metal, alkaline-earth metal or optionally substituted ammonium salts of higher fatty acids ($C_{10}$–$C_{22}$), for example the sodium or potassium salts of oleic or stearic acid, or of natural fatty acid mixtures, which can be obtained for example from coconut oil or tallow oil. Also to be mentioned as tensides are the fatty acid-methyl-taurine salts.

So-called synthetic tensides are however more frequently used, particularly fatty sulfonates, fatty sulfates, sulfonated benzimidazole derivatives or alkylarylsulfonates.

The fatty sulfonates or sulfates are as a rule in the form of alkali metal, alkaline-earth metal or unsubstituted or substituted ammonium salts, and they generally contain an alkyl group having 8 to 22 C atoms, 'alkyl' including also the alkyl moiety of acyl groups, for example the Na or Ca salt of ligninsulfonic acid of dodecylsulfuric acid ester or of a fatty alcohol sulfate mixture produced from natural fatty acids. Included among these are the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols. Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples of nonionic tensides which may be mentioned are: nonylphenol-polyethoxyethanols, castor oil polyblycol ethers, polypropylene/polyethylene oxide adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyl-trimethyl ammonium chloride or benzyldi-(2-chloroethyl)-ethylammonium bromide.

The tensides customarily used in formulation practice are described, inter alia, in the following publications:

"McCutcheon's Detergents and Emulsifiers Annual", MC Publishing Corp., Ridgewood, N.J., 1981;

Dr. Helmut Stache "Tensid-Taschenbuch" (Tenside Manual), Carl Hanser Verlag, Munich/Vienna, 1981.

The pesticidal preparations contain as a rule 0.1 to 99%, particularly 0.1 to 95%, of active ingredient of the formula I, or of combinations of this active ingredient with other insecticides or acaricides, 1 to 99.9% of a solid or liquid additive, and 0 to 25%, especially 0.1 to 20%, of a tenside. Whereas commercial products are preferably in the form of concentrated compositions, the products employed by the end-user are as a rule preparations having considerably lower concentrations of active ingredient.

The compositions can also contain further additives, such as stabilisers, antifoaming agents, viscosity regulators, binders and adhesives, as well as fertilisers or other active ingredients for obtaning special effects.

FORMULATION EXAMPLES FOR LIQUID ACTIVE INGREDIENTS OF THE FORMULA I OR COMBINATIONS OF THESE ACTIVE INGREDIENTS WITH OTHER INSECTICIDES OR ACARICIDES (%=PERCENT BY WEIGHT)

| 1. Emulsion concentrates | (a) | (b) | (c) |
|---|---|---|---|
| active ingredient or active-ingredient combination | 25% | 40% | 50% |
| calcium dodecylbenzenesulfonate | 5% | 8% | 6% |
| castor-oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of the concentration required can be produced from such concentrates by dilution with water.

| 2. Solutions | (a) | (b) | (c) | (d) |
|---|---|---|---|---|
| active ingredient or active-ingredient combination | 80% | 10% | 5% | 95% |
| ethylene glycol monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160-190° C.) | — | — | 94% | — |

The solutions are suitable for application in the form of very fine drops.

| 3. Granulates | (a) | (b) |
|---|---|---|
| active ingredient or active-ingredient combination | 5% | 10% |
| kaolin | 94% | — |
| highly dispersed silicic acid | 1% | — |
| attapulgite | — | 90% |

The active ingredient or the active-ingredient combination is dissolved in methylene chloride, the solution is sprayed onto the carrier, and the solvent is subsequently evaporated off in vacuo.

| 4. Dusts | (a) | (b) |
|---|---|---|
| active ingredient or active-ingredient combination | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient or active-ingredient combination.

FORMULATION EXAMPLES FOR SOLID ACTIVE INGREDIENTS OF THE FORMULA I OR COMBINATIONS OF THESE ACTIVE INGREDIENTS WITH OTHER INSECTICIDES OR ACARICIDES (%=PERCENT BY WEIGHT)

| 5. Wettable powders | (a) | (b) | (c) |
|---|---|---|---|
| active ingredient or active-ingredient combination | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient or the active-ingredient combination is well mixed with the additives, and the mixture is thoroughly ground in a suitable mill. Wettable powders which can be diluted with water to give suspensions of the concentration required are obtained.

| 6. Emulsion concentrate | |
|---|---|
| active ingredient or active-ingredient combination | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained form this concentrate by dilution with water.

| 7. Dusts | (a) | (b) |
|---|---|---|
| active ingredient or active-ingredient combination | 5% | 8% |
| talcum | 95% | — |
| kaolin | — | 92% |

Dusts ready for use are obtained by mixing the active ingredient or active-ingredient combination with the carriers and grinding the mixture in a suitable mill.

| 8. Extruder granulate | |
|---|---|
| active ingredient or active-ingredient combination | 10% |
| sodium lignin sulfonate | 2% |
| carboxymethylcellulose | 1% |
| kaolin | 87% |

The active ingredient is mixed and ground with the additives, and the mixture is moistened with water. The mixture is extruded, granulated, and subsequently dried in a stream of air.

| 9. Coated granules | |
|---|---|
| active ingredient or active-ingredient combination | 3% |
| polyethylene glycol (M.W. 200) | 3% |
| kaolin | 94% |

The finely ground active ingredient or the active-ingredient combination is evenly applied, in a mixer, to the kaolin moistened with polyethylene glycol. Dust-free coated granules are obtained in this manner.

| 10. Suspension concentrate | |
|---|---|
| active ingredient or active-ingredient combination | 40% |
| ethylene glycol | 10% |
| nonylphenol-polyethylene glycol (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or the active-ingredient combination is intimately mixed with the additives. There is thus obtained a suspension concentrate from which can be prepared, by dilution with water, suspensions of the concentration required.

EXAMPLE 1

Production of N-ethoxycarbonyl-N-2-(4-phenoxyphenoxy)-ethyl-oxamic acid methyl ester 7.5 g of 2-(4-phenoxyphenoxy)-ethyl-carbamic acid ethyl ester are dissolved in 80 ml of ethylene chloride. To this solution are added 5.0 g of oxalic acid monomethyl ester chloride, and the reaction mixture is stirred for 6 hours under mild refluxing conditions. The mixture is subsequently concentrated by evaporation, and the residue is taken up in dichloromethane. This solution is washed with cold water, dried over sodium sulfate and finally concentrated by evaporation to one fifth. Chromatography on silica gel with dichloromethane as eluant thus yields the compound of the formula compound No. 1.1

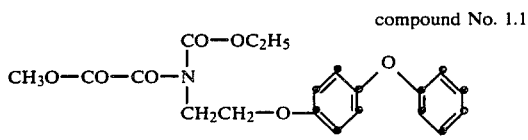

as light-yellow oil having a refractive index of $n_D^{20} = 1.5419$.

There are obtained by a procedure analogous to that described above also the following compounds:

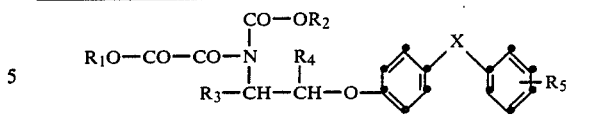

| Comp. No. | $R_1$ | $R_2$ | $R_3$ | $R_4$ | $R_5$ | X | Physical data |
|---|---|---|---|---|---|---|---|
| 1.2 | $CH_3$ | $CH_3$ | H | H | H | O | $n_D^{20}$:1.5486 |
| 1.3 | $CH_3$ | $C_2H_5$ | H | H | H | S | $n_D^{20}$:1.5694 |
| 1.4 | $C_2H_5$ | $C_2H_5$ | H | H | H | O | $n_D^{20}$:1.5369 |

EXAMPLE 2

Production of N-ethyl-N-2-(4-phenoxyphenoxy)ethoxycarbonyl-oxamic acid ethyl ester 9.0 g of N-ethyl-carbamic acid-2-(4-phenoxyphenoxy)ethyl ester are dissolved in 90 ml of ethylene chloride. To this solution are added 9.6 g of oxalic acid monoethyl ester chloride, and stirring is maintained for 10 hours under mild refluxing conditions. The cooled reaction mixture is then poured into 200 ml of ice-water, and the organic phase is separated. This is washed with cold water, dried over sodium sulfate, concentrated by evaporation and taken up in dichloromethane. Chromatography on silica gel with dichloromethane as the eluant thus yields the compound of the formula compound No. 2.1

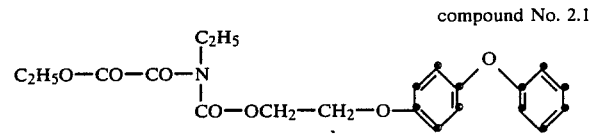

in the form of white crystals having a m.p. of 56°–58° C.

There are obtained by a procedure analogous to that described above also the following compounds:

| Comp. No. | $R_1$ | $R_2$ | $R_3$ | $R_4$ | $R_5$ | X | Physical data |
|---|---|---|---|---|---|---|---|
| 2.2 | $CH_3$ | $CH_3$ | H | H | H | O | $n_D^{20}$:1.5508 |
| 2.3 | $CH_3$ | $C_2H_5$ | H | H | H | O | m.p. 63–64° C. |
| 2.4 | $CH_3$ | $C_2H_5$ | H | H | H | S | m.p. 49–51° C. |
| 2.5 | $C_2H_5$ | $CH_3$ | H | H | H | O | m.p. 60–62° C. |
| 2.6 | $C_2H_5$ | $C_2H_5$ | H | H | H | S | $n_D^{20}$:1.5632 |
| 2.7 | $CH_3$ | $C_2H_5$ | H | H | 4-Cl | O | $n_D^{20}$:1.5494 |
| 2.8 | $CH_3$ | $C_2H_5$ | $CH_3$ | H | H | O | $n_D^{20}$:1.5348 |
| 2.9 | $CH_3$ | $C_2H_5$ | H | $CH_3$ | H | O | $n_D^{20}$:1.5376 |
| 2.10 | $CH_3$ | $C_2H_5$ | H | $CH_3$ | H | S | $n_D^{20}$:1.5653 |
| 2.11 | $CH_3$ | $C_4H_9$—n | H | H | H | O | $n_D^{21}$:1.5342 |

In the Biological Examples given in the following, a good action signifies that the desired effect has been obtained to the extent of at least 50 to 60%.

EXAMPLE 3

Action against *Laspeyresia pomonella* (eggs)

Deposited *Laspeyresia pomonella* eggs, not more than 24 hours old, are immersed on filter paper for 1 minute in acetonic/aqueous solutions containing 0.75, 12.5, 100 and 400 ppm, respectively, of the active ingredient to be tested. After the drying of the solution on the eggs, there are laid out in Petri dishes and kept at a temperature of 28° C. The percentage hatching rate from the treated eggs is evaluated after 6 days.

The compounds Nos. 1.1, 1.2, 1.3, 1.4, 2.2, 2.4, 2.5 and 2.7 exhibit a 100% action (mortality) in the above test at an active-ingredient concentration as low as 0.75 ppm.

EXAMPLE 4

Effect on reproduction of *Anthonomus grandis*

Adult *Anthonomus grandis*, which have been hatched no longer than 24 hours, are transferred, in groups each of 25 beetles, to cages having lattice walls. The cages containing the beetles are then immersed for 5 to 10 seconds in an acetonic solution containing 1.0% by weight of the active ingredient to be tested.

After the beetles are again dry, they are placed, for copulation and oviposition, into covered dishes containing feed. Deposited eggs are flushed out with running water two to three times weekly; they are counted, disinfected by being placed for two to three hours into an aqueous disinfectant, and then deposited into dishes containing a suitable larval diet. An examination is made after 7 days to determine whether larvae have developed from the deposited eggs.

In order to ascertain the duration of the reproduction-influencing effect of the active ingredients tested, the oviposition of the beetles is observed during a period of about four weeks. The evaluation is on the basis of the reduction in the number of eggs deposited and larvae hatched in comparison with that in the case of untreated control specimens.

Compounds according to Examples 1 and 2 exhibit a good reproduction-influencing effect in the above test.

What is claimed is:

1. A compound of the formula

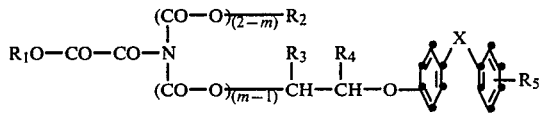

wherein
$R_1$ is $C_1$-$C_{10}$-alkyl,
$R_2$ is $C_1$-$C_4$-alkyl,
$R_3$ and $R_4$ are each hydrogen or methyl,
$R_5$ is hydrogen, halogen, $C_1$-$C_4$-alkyl, $C_1$-$C_4$-alkoxy $C_1$-$C_4$-alkylthio or $C_1$-$C_4$-haloalkyl,
X is oxygen or sulfur, and
m is 1 or 2.

2. A compound of claim 1, wherein
$R_1$ is $C_1$-$C_6$-alkyl,
$R_2$ is $C_1$-$C_4$-alkyl,
$R_3$ and $R_4$ are each hydrogen or methyl,
$R_5$ is hydrogen or halogen,
X is oxygen or sulfur, and
m is 1 or 2.

3. A compound of claim 2, wherein
$R_1$ and $R_2$ are each $C_1$-$C_4$-alkyl,
$R_3$ and $R_4$ are each hydrogen or methyl,
$R_5$ is hydrogen or chlorine,
X is oxygen or sulfur, and
m is 1 or 2.

4. A compound of claim 3, wherein
$R_1$ and $R_2$ are each methyl or ethyl,
$R_3$, $R_4$ and $R_5$ are each hydrogen,
X is oxygen, and
m is 2.

5. A compound of claim 3 of the formula

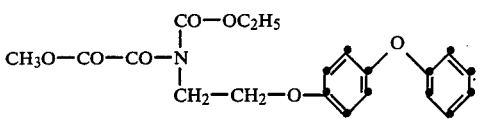

6. A compound of claim 3 of the formula

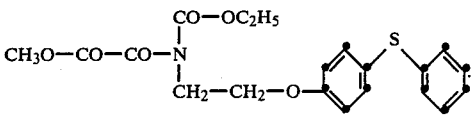

7. A compound of claim 3 of the formula

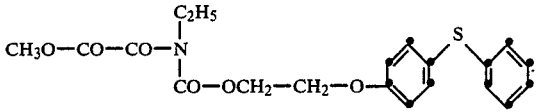

8. An arthropodicidal composition containing an arthropodicidally effective amount of a compound of the formula

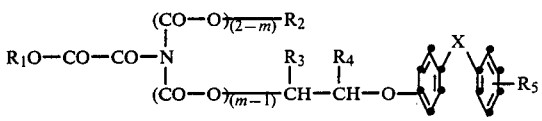

wherein
$R_1$ is $C_1$-$C_{10}$-alkyl,
$R_2$ is $C_1$-$C_4$-alkyl,
$R_3$ and $R_4$ are each hydrogen or methyl,
$R_5$ is hydrogen, halogen, $C_1$-$C_4$-alkyl, $C_1$-$C_4$-alkoxy, $C_1$-$C_4$-alkylthio or $C_1$-$C_4$-haloalkyl,
X is oxygen or sulfur, and
m is 1 or 2,
together with a suiable carrier.

9. A method of controlling arthropodal pests on animals and plants, which method comprises applying thereto or to the locus thereof an arthropodically effective amount of a compound of the formula

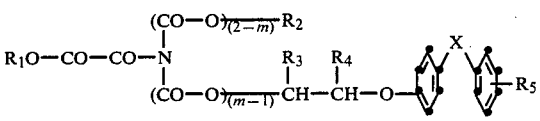

wherein
$R_1$ is $C_1$-$C_{10}$-alkyl,
$R_2$ is $C_1$-$C_4$-alkyl,
$R_3$ and $R_4$ are each hydrogen or methyl,
$R_5$ is hydrogen, halogen, $C_1$-$C_4$-alkyl, $C_1$-$C_4$-alkoxy, $C_1$-$C_4$-alkylthio or $C_1$-$C_4$-haloalkyl,
X is oxygen or sulfur, and
m is 1 or 2.

10. A method of claim 9 for controlling insects and arachnids.

11. A method of claim 10 for controlling larvae and eggs of phytophagous insects and mites.